United States Patent [19]

Loh

[11] Patent Number: 4,824,470
[45] Date of Patent: Apr. 25, 1989

[54] 2-(1-(5-HALOTHIENYLMETHOX-YIMINO)ETHYL-3-HYDROXY-5-(TETRAHY-DRO-2H-THIOPYRANYL)-CYCLOHEX-2-EN-1-ONE HERBICIDES

[75] Inventor: William Loh, Petaluma, Calif.

[73] Assignee: Chevron Research Company, San Francisco, Calif.

[21] Appl. No.: 101,321

[22] Filed: Sep. 25, 1987

[51] Int. Cl.[4] .................... C07D 409/02; A01N 43/02
[52] U.S. Cl. ............................................ 71/90; 549/13
[58] Field of Search ............................... 549/13; 71/90

[56] References Cited

U.S. PATENT DOCUMENTS

| | | | |
|---|---|---|---|
| 4,432,786 | 2/1984 | Loh | 71/90 |
| 4,596,877 | 6/1986 | Becker et al. | 71/90 |
| 4,624,696 | 11/1986 | Keil et al. | 71/90 |

*Primary Examiner*—Jane T. Fan
*Attorney, Agent, or Firm*—S. R. La Paglia; R. C. Gaffney; L. S. Squires

[57] ABSTRACT

2-[1-[(5-chlorothien-2-yl)methoxyimino]ethyl]-3-hydroxy-5- (tetrahydro-2H-thiopyran-3-yl)-cyclohex-2-en-1-one and 3-alkanoyloxy thereof derivatives are disclosed. The compounds exhibit pre- and post-emergent phytotoxicity and are useful as selective post-emergent herbicides against grasses.

19 Claims, No Drawings

2-(1-(5-HALOTHIENYLMETHOXYIMINO)ETHYL-3-HYDROXY-5-(TETRAHYDRO-2H-THIOPYRANYL)-CYCLOHEX-2-EN-1-ONE HERBICIDES

BACKGROUND OF THE INVENTION

This invention relates to certain 2-[1-(halothienylmethoxyimino)ethyl]-3-hydroxy-5-(tetrahydro-2H-thiopyranyl)-cyclohex-2-en-1-one and salts thereof and to the use of such compounds as herbicides.

U.S. Pat. No. 4,624,696, issued Nov. 25, 1986, discloses compounds having the formula:

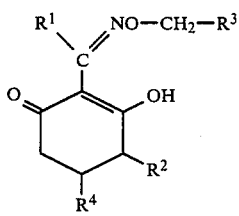

wherein $R^1$ is alkyl of 1 to 4 carbon atoms, $R^2$ is hydrogen or alkoxycarbonyl of 2 to 5 carbon atoms, $R^3$ is a 5-membered heterocyclic structure which contains 1 to 3 heteroatoms from the group consisting of N, O, and S and may contain 1 or 2 double bonds and 1 or 2 substituents from the group consisting of $C_1$-$C_4$-alkyl, $C_1$-$C_4$-alkoxy, halogen, trifluoromethyl, $C_1$-$C_4$-alkoxymethyl, $C_1$-$C_4$-alkylthiomethyl, vinyl and phenyl, and $R^4$ is a 5-membered to 7-membered heterocyclic structure which contains one heteroatom or ring member, or two identical or different heteroatoms or ring members, from the group consisting of N, O, S, SO, and $SO_2$, may contain 1, 2, or 3 double bonds and is unsubstituted or substituted by not more than 2 alkyl or alkoxy groups, each of 1 to 4 carbon atoms, or is a radical of the formula II

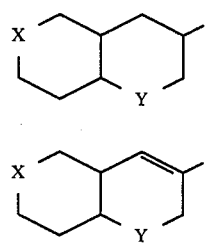

where X and Y are each N, O, S, SO, or $SO_2$, and salts of these compounds.

This patent teaches that $R^1$ is preferably a radical having two or three carbon atoms. The patent describes the compounds as exhibiting herbicidal activity against grasses and safe with respect to a number of enumerated crops.

The patent also teaches that these compounds exhibit herbicidal activity against grasses and are safe with respect to a number of crops.

U.S. Pat. No. 4,596,877 discloses compounds having the formula

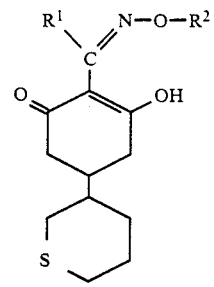

wherein $R^1$ is $C_1$-$C_4$ alkyl and $R^2$ is $C_3$-$C_5$ chloroalkenyl. $R^1$ is preferably ethyl or propyl.

The compounds are described as being effective to remove grasses while being safe for a number of crops.

My prior U.S. Pat. No. 4,432,786 discloses compounds having the following formulas and their salts:

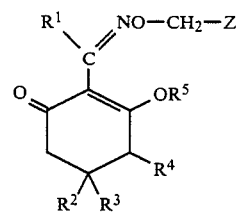

wherein
$R^1$ is hydrogen or lower alkyl;
$R^2$ and $R^3$ are independently selected from the group consisting of hydrogen, lower alkyl, aryl having 6 through 10 carbon atoms (preferably phenyl), substituted aryl having 6 through 10 carbon atoms (preferably phenyl) and 1 through 4 substituents (preferably 1 or 2) independently selected from the group consisting of fluoro, chloro, bromo, iodo, or trifluoromethyl;
$R^4$ is hydrogen or alkoxycarbonyl having 2 through 4 carbon atoms;
$R^5$ is hydrogen, or an acyl group having 1 through 12 carbon atoms; and
Z is a group having the formula:

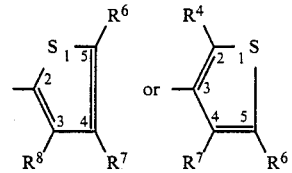

wherein $R^6$, $R^7$, and $R^8$ are independently selected from the group of hydrogen, halo, nitro, alkyl having 1 through 4 carbon atoms, alkoxy having 1 through 4 carbon atoms, or trifluoromethyl.

In the aforementioned patent, I describe the compounds wherein $R^1$ is ethyl or propyl and/or Z is a chlorothienyl as preferred. The compounds are described exhibiting excellent grass herbicidal activity.

SUMMARY OF THE INVENTION

It has now been discovered that certain of the compounds (i.e., see Formula I below wherein R is hydrogen) encompassed within the broad generic disclosure of U.S. Pat. No. 4,624,696, exhibit superior herbicidal activity as compared with others. The outstanding herbicidal activity possessed by the present compounds rarely exists and cannot be predicted beforehand. The outstanding herbicidal activity possessed by this compound is particularly surprising because the substituent corresponding to the $R^1$ position in the compounds discussed above is methyl and generally in this class of compounds the $R^1$ is ethyl and propyl compounds are superior herbicides to their $R^1$ is methyl homologs. The compound of Formula I hereinbelow wherein R is H is not only an excellent herbicide against grasses it is also surprisingly more phytotoxic than both the $R^1$ is ethyl and $R^1$ is propyl homologs. The 3-alkanoyl (i.e., Formula I,

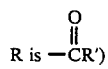
R is —ĈR')

derivative of this compound are also excellent herbicides.

The present compounds exhibit both pre-emergence and post-emergence phytotoxicity with respect to grasses and exhibit excellent especially post-emergence herbicidal activity against Bermudagrass, foxtail, crabgrass, volunteer corn, volunteer sorghum, barnyardgrass, broad-leaf signalgrass, goosegrass, red rice, sprangletop, seedling Johnsongrass and Rhizome Johnsongrass. The compounds of Formula I, and their salts, are very useful for controlling grasses and are especially useful for controlling grassy weeds in sugar beet crops.

The compounds of Formula I have also been found to exhibit plant growth regulating activity providing excellent control of tobacco suckers as is more fully described in commonly assigned application Ser. No. 101,324, filed on even date herewith. Moreover, the R is alkanoyl compounds have surprisingly been found to be superior to the R is hydrogen compounds for controlling tobacco suckers.

The compound of the present invention can be represented by the following formula:

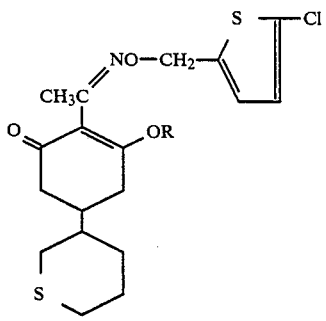

wherein R is hydrogen or

wherein R' is alkyl having 1 through 10 carbon atoms, preferably 1 through 7 carbon atoms.

The invention also comprises compatible salts of the compound of Formula I.

As is well recognized, compounds of the nature of Formula (I) exist as tautomers. The compounds also have two asymmetric carbon atoms and can also exist as optical isomers. The above formula is intended to encompass the respective tautomeric forms as well as the individual optical isomers as well as mixtures thereof and the respective tautomers and optical isomers as well as mixtures thereof are encompassed within the invention.

In a further aspect the invention provides a herbicidal composition comprising a compatible carrier and a herbicidally effective amount of the compound(s) of the invention or mixtures thereof.

The present invention also provides a method for preventing or controlling the growth of unwanted grassy vegetation, which comprises treating the growth medium and/or the foliage of such vegetation with a herbicidally effective amount of the compound(s) of the invention or mixtures thereof.

The present invention also provides a method for regulating plant growth which comprises treating the growth medium and/or the foliage of such vegetation with a plant growth regulating effective amount of the compound(s) of the invention or mixtures thereof, effective to alter the normal growth pattern of said plants.

The present invention also provides chemical intermediates and processes for preparing the compounds of the invention.

The invention will be further described hereinbelow.

FURTHER DESCRIPTION OF THE INVENTION AND THE PREFERRED EMBODIMENTS

In terms of weed control the preferred compounds are those wherein R is hydrogen or acetyl. In terms of tobacco sucker control, which is more fully described in commonly assigned copending application Ser. No. 101,324 filed on even date herewith, the preferred compounds are those wherein R is alkanoyl especially acetyl and propionyl.

The compound of Formula (I) can be conveniently prepared by the following schematically represented process:

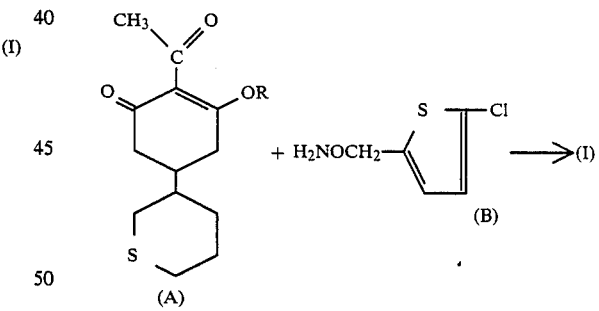

wherein R is as defined hereinabove.

This process can be conveniently effected by contacting Compound (A) with (5-chlorothien-2-yl)methoxyamine (B), under reactive conditions preferably in an inert organic solvent.

Typically, this process is conducted at temperatures in the range of about from 0° to 80° C., preferably about from 20° to 40° C., for about from 1 to 48 hours, preferably about from 4 to 12 hours, using about from 1 to 2, preferably 1.05 to 1.2 moles of (5-chlorothien-2-yl)methoxyamine (B) per mole of Compound (A). Suitable inert organic solvents which can be used include, for example, lower alkanols, e.g., methanol, ethanol; ethers, e.g., ethyl ether; methylene chloride. Two-phase water and immiscible organic solvent (e.g., hexane), and mixtures thereof can also be used as the reaction medium.

(5-chlorothien-2-yl)methoxyamine is a known compound and can be prepared via known procedures, such as, for example, described in my prior U.S. Pat. No. 4,432,786. The (5-chlorothien-2-yl)methoxyamine reactant can be conveniently provided by neutralizing its hydrochloride salt in situ with an alkali metal alkoxide. The starting materials of Formula (A) wherein R is hydrogen is also a known compound and can be prepared via the general procedure described in U.S. Pat. Nos. 4,624,696 and 4,596,877.

The compound of Formula A wherein R is alkanoyl can be conveniently prepared by acylating the compound of the R is hydrogen compound of Formula A:

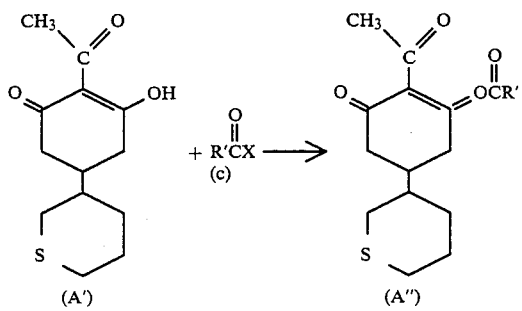

wherein R' is lower alkyl having 1 through 10 carbon atoms and X is chloro or bromo preferably chloro.

This process can be effected by contacting Compound A' with the appropriate acyl halide under reactive conditions preferably in an inert organic solvent and preferably in the presence of a scavenger base.

Typically this process is conducted at temperatures in the range of about from $-78°$ to $100°$ C., preferably $0°$ to $25°$ C. for about from 1 to 48 hours using about from 1 to 5 moles, preferably 1 to 1.2 moles of acyl halide (c) per mole of Compound A'. Where a scavenger base is used typically about from 1 to 5, preferably 1 to 1.2 moles of scavenger base is used per mole of Compound A'. Suitable scavenger bases which can be used include, for example, triethylamine, pyridine, methylpyridine, 2,4-lutidine, and the like. Suitable solvents which can be used include, for example methylene chloride, chloroform, ethyl acetate, acetonitrile, diethyl ether, tetrahydrofuran, and the like.

The compounds of Formula I wherein R is alkanoyl can also be prepared by acylating the compound of Formula I wherein R is hydrogen. For example, the acylation can be effected using the appropriate acyl halide using substantially the same conditions as described above with respect to the acylation of Compound A'. Other acylating agents could also be used in either case such as, for example, acyl anhydrides.

The compatible salts of Formula (I) can be prepared by conventional procedures, for example, via the reaction of the compound of Formula I, wherein R is hydrogen, with a base, such as, for example, sodium hydroxide, potassium hydroxide and the like, having the desired cation. Additional variations in the salt cation can also be effected via ion exchange with an ion exchange resin having the desired cation.

The term "compatible salts" refers to salts which do not significantly adversely alter the herbicidal properties of the parent compound. Suitable salts include cation salts such as, for example, the cation salts of lithium, sodium, potassium, alkali earth metals, copper, zinc, ammonia, quaternary ammonium salts, and the like.

General Process Conditions

The reaction product can be recovered from its reaction product mixture by any suitable separation and purification procedure, such as, for example, chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures. Geometric isomers can be separated by conventional separation procedures which depend upon differences in physical properties between the geometric isomers. However, it is generally preferable to use the desired isomeric starting material in the reaction.

Definitions

Unless expressly stated to the contrary, the following terms as used herein have the following meanings.

The term "alkyl" refers to both straight chain and branched chain alkyl groups such as, for example, methyl, ethyl, propyl, isopropyl, butyl, t-butyl, pentyl, 2-methylpentyl, hexyl, octyl, and the like.

The term "room temperature" or "ambient temperature" refers to about $20°$-$25°$ C.

Utility

The compounds of Formula (I) and their salts exhibit both pre- and post-emergent herbicidal activity and exhibit especially good herbicidal activity against grasses. The compounds exhibit especially good phytotoxicity against foxtail, Bermudagrass, crabgrass, rhizome, Johnsongrass and volunteer corn. These weed species are generally very difficult to control and hence, the present compounds provide a significant advantage which respect to the control of such weeds.

Generally, for post-emergent applications, the herbicidal compounds are applied directly to the foliage or other plant parts. For pre-emergence applications, the herbicidal compounds are applied to the growth medium, or prospective growth medium, for the plant. The optimum amount of the herbicidal compound or composition will vary with the particular plant species, and the extent of plant growth, if any, and the particular part of the plant which is contacted and the extent of contact. The optimum dosage can also vary with the general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having high concentrations designed for dilution prior to application. The carrier can be a solid, liquid, or aerosol. The actual compositions can take the form of granules, powders, dusts, solutions emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for preemergence application agents which reduce the leachability of the compound or otherwise enhance soil stability. Crop oils, such as, for example, soybean oils, paraffin oils and olefinic oils, are especially advantageous as carriers or additives in that they enhance phytotoxicity. Various other adjuvants available to enhance the phytotoxicity of oximenychlohexanedione class of herbicides can also be advantageously used.

The composition can also contain various compatible adjuvants, stabilizers, conditioners, insecticides, fungicides, and if desired, other herbicidally active compounds.

One convenient concentrate formulation which can be used comprises 23-27% by weight of the active herbicide of the invention, 2 to 4% by weight of an emulsifier, for example, calcium alkylbenzene sulfonates, octylphenolethoxylate, etc., or mixtures thereof, and about 70-75% organic solvent, for example, xylene, etc. The concentrate is mixed with water and preferably a crop oil prior to application and applied as a water emulsion containing about 0.5 to 2% of a crop oil, for example, soybean oils, and paraffinic oils and olefinic oils. Conveniently, the herbicide is applied as water emulsion containing about 0.02-0.6 wt. %, preferably 0.07-0.15 wt. % of the herbicide, of the invention; about 0.001-0.01 wt. % of an emulsifier; about 0.08-2.5 wt. % of an organic solvent and about 95 to 99 wt. % water. Preferably, the composition also contains about 0.25 to 2 wt. % of a crop oil. The application composition can be conveniently prepared by mixing the concentrate formulation with about ¼ to ½ the desired amount of water. Then admixing the crop oil and then adding the remaining amount of water. Mixtures of different crop oils can also be used. If no crop oil is used, then the water and concentrate formulation are simply admixed together.

A further understanding of the invention can be had in the following non-limiting Preparation(s) and Example(s). Wherein unless expressly stated to the contrary, all temperatures and temperature ranges refer to the Centigrade system and the term "ambient" or "room temperature" refers to about 20°-25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Unless otherwise stated where given, proton-magnetic resonance spectrum (p.m.r. or NMR) were determined at 60 mHz, signals are assigned as singlets (s), broad singlets (bs), doublets (d), double doublets (dd), triplets (t), double triplets (dt) quartets (q), and multiplets (m); and cps refers to cycles per second. Also where necessary examples are repeated to provide additional starting material for subsequent examples.

EXAMPLES

Example 1

2-[1-[(5-chlorothien-2-yl)methoxyimino]ethyl]-3-hydroxy-5-(tetrahydro-2H-thiopyran-3-yl)cyclohex-2-en-1-one A solution containing 5.1 g (0.020 mol) of 2-acetyl-3-hydroxy-5-(tetrahydro-2H-thiopyran-3-yl)cyclohex-2-en-1-one and 3.4 g (0.021 mol) of (5-chlorothien-2-yl)methoxyamine in 200 ml of ethanol was stirred overnight (about 14 hours) at room temperature and then evaporated to remove ethanol. The concentrate was diluted with 150 ml of methylene chloride and then washed with 100 ml of water and then with 100 ml of saturated aqueous sodium chloride solution. The washed methylene chloride solution was dried over anhydrous magnesium sulfate and then evaporated to dryness under reduced pressure to afford a white solid. Recrystallation of this solid with absolute ethanol afforded 7.6 g of the title compound, m.p. 154°-155° C. cl EXAMPLE 2

Sodium 2-[1-[(5-chlorothien-2-yl)methoxyimino]ethyl]-3-oxo-5-(tetrahydro-2H-thiopyran-3-yl)-cyclohex-1-en-1-olate This example illustrates a procedure which can be used to prepare the title compound.

A solution containing 0.01 mol of sodium hydroxide dissolved in 2 ml of water is added to a solution containing 0.01 mol of 2-[1-[(5-chlorothien-2-yl)methoxyimino]ethyl]-3-hydroxy-5-(tetrahydro-2H-thiopyran-3-yl)-cyclohex-2-en-1-one at room temperature. After the reaction is completed, the solvents are evaporated off under vacuum affording the 1-hydroxy sodium salt of 2-[1-[(5-chlorothien-2-yl)methoxyimino]ethyl]-3-hydroxy-5-(tetrahydro-2H-thiopyran-3-yl)-cyclohex-2-en-1-one.

EXAMPLE 3

3-Acetyloxy-2-[1-[(5-chlorothien-2-yl)methoxyimino]ethyl]-5-(tetrahydro-2H-thiopyran-3-yl)-cyclohex-2-en-1-one In this example, 0.52 g (5.1 mmol) of triethylamine was admixed to a solution containing 1.46 g (3.7 mmol) of 2-[1-[(5-chlorothien-2-yl)methoxyimino]ethyl]-5-(tetrahydro-2H-thiopyran-3-yl)-cyclohexane-1,3-dione in 30 ml of methylene chloride at room temperature (about 20°–25° C.) followed by the dropwise addition of 0.35 g (4.4 mmol) of acetyl chloride. The mixture was stirred at room temperature overnight (about 14 hours) and then washed with saturated aqueous sodium bicarbonate solution, followed by saturated sodium chloride solution. The washed extract was dried over anhydrous magnesium sulfate and concentrated under reduced pressure. The product was purified by column chromatography on silica gel to afford 1.0 g of the title compound as a yellow oil; IR (neat) 1775 cm$^{-1}$; $^1$H NMR spectrum (90 MHz CDCl$_3$) δ1.00–2.60 (m, 14H), 1.93 (s, 3H), 2.00 (s, 3H), 5.07 (s, 2H) 6.73 (s, 2H).

Similarly, by applying the above procedure using the appropriate acyl chloride the following compounds can be prepared:

3-propionyloxy-2-[1-[5-chlorothien-2-yl)methoxyimino)ethyl]-5-(tetrahydro-2H-thiopyran-3-yl)-cyclohex-2-en-1-one;

3-butyryloxy-2-[1-[(5-chlorothien-2-yl)methoxyimino]ethyl]-5-(tetrahydro-2H-thiopyran-3-yl)-cyclohex-2-en-1-one;

3-isobutyryloxy-2-[1-[(5-chlorothien-2-yl)methoxyimino]ethyl]-5-(tetrahydro-2H-thiopyran-3-yl)-cyclohex-2-en-1-one;

3-valeryloxy-2-[1-[(5-chlorothien-2-yl)methoxyimino]ethyl]-5-(tetrahydro-2H-thiopyran-3-yl)-cyclohex-2-en-1-one;

3-isovaleryloxy-2-[1-[(5-chlorothien-2-yl)methoxyimino]ethyl]-5-(tetrahydro-2H-thiopyran-3-yl)-cyclohex-2-en-1-one;

3-pivaloyloxy-2-[1-[(5-chlorothien-2-yl)methoxyimino]ethyl]-5-(tetrahydro-2H-thiopyran-3-yl)-cyclohex-2-en-1-one;

3-hexanoyloxy-2-[1-[(5-chlorothien-2-yl)methoxyimino]ethyl]-5-(tetrahydro-2H-thiopyran-3-yl)-cyclohex-2-en-1-one; and 3-heptanoyloxy-2-[1-[(5-chlorothien-2-yl)methoxyimino]ethyl]-5-(tetrahydro-2H-thiopyran-3-yl)-cyclohex-2-en-1-one.

EXAMPLE 4

2-Acetyl-3-acetyloxy-5-(tetrahydro-2H-thiopyran-3-yl)-cyclohex-2-en-1-one

The title compound can be prepared by the following procedure:

0.82 g (10.5 mmol) of acetyl chloride is added dropwise to a stirred solution of 2.54 g (10.0 mmol) of 2-acetyl-3-hydroxy-5-(tetrahydro-2H-thiopyran-3-yl)-cyclohex-2-en-1-one and 1.06 g (10.5 mmol) of triethylamine in 50 ml of dichloromethane. The mixture is stirred overnight at room temperature, and then is poured into 100 ml of ice-cold water. The organic layer is separated and washed with 20 ml of dilute sodium bicarbonate solution, followed by 50 ml of saturated sodium chloride solution. The washed extract is then dried over anhydrous magnesium sulfate and concentrated under reduced pressure. The product can be purified by column chromatography employing tetrahydrofuran-hexane (1:2 by volume) as eluent to afford the title compound.

EXAMPLE 5

3-Acetyloxy-2-[1-[(5-chlorothien-2-yl)methoxyimino]ethyl]-5-(tetrahydro-2H-thiopyran-3-yl)-cyclohex-2-en-1-one The title compound can be prepared by the following procedure:

0.34 g (2.0 mmol) of (5-chlorothien-2-yl)methoxyamine is added to a stirred solution of 0.59 g (2.0 mmol) of 2-acetyl-3-acetyloxy-5-(tetrahydro-2H-thiopyran-3-yl)-cyclohex-2-en-1-one in 10 ml of absolute ethanol. After stirring overnight at room temperature, the reaction mixture is concentrated under reduced pressure. The resulting residue is diluted with 25 ml of dichloromethane and washed twice with 10 ml of saturated sodium chloride solution. The washed extract is then dried over anhydrous magnesium sulfate and evaporated under reduced pressure. The product can then be purified by column chromatography employing tetrahydrofuran-hexane (1:2 by volume) as eluent to afford the title compound.

EXAMPLE 6

In this example, the title compound of Example 1, i.e., 2-[1-[(5-chlorothien-2-yl)methoxyimino]ethyl]-3-hydroxy-5-(tetrahydro-2H-thiopyran-3-yl)-cyclohex-2-en-1-one and its $R^1$ is ethyl and propyl homologs, i.e., 2-[1-[(5-chlorothien-2-yl)methoxyimino]propyl]-3-hydroxy-5-(tetrahydro-2H-thiopyran-3-yl)-cyclohex-2-en-1-one (C-1) and 2-[1-[(5-chlorothien-2-yl)methoxyimino]butyl]-3-hydroxy-5-(tetrahydro-2H-thiopyran-3-yl)-cyclohex-2-en-1-one (C-2); were tested, side-by-side using the procedures described hereinbelow, for pre-emergent and post-emergent phytotoxic activity against a variety of grasses and broad-leaf plants.

Pre-Emergent Herbicide Test

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/l. Dilutions were made as needed to arrive at the desired spray concentrations.

Seeds of the test vegetation were planted in a pot of soil and the test solution was sprayed uniformly onto the soil surface at the test compound dosage indicated in Table 1. Three replicate pots were used per species and rate. The pots were watered and placed in a greenhouse. The pots were watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests are expressed as an average of the results for the three replicates and are summarized in Table 1.

Post-Emergent Herbicidal Test

The test compound was formulated in the same manner as described above for the pre-emergent test. This formulation was uniformly sprayed on 2 similar pots containing plants 2 to 3 inches tall (except wild oats, soybean and barnyardgrass which were 3 to 4 inches tall) (approximately 15 to 25 plants per pot) at the test compound dose indicated in Table 2. After the plants had dried, they were placed in a greenhouse and then watered intermittently at their bases as needed. The plants were observed periodically for phytotoxic effects and physiological and morphological responses to the treatment. Three replicate pots were used per species and test rate. After 3 weeks, the herbicidal effectiveness of the compound was rated based on these observations. A 0-to-100 scale was used, 0 representing no phytotoxicity, 100 representing complete kill. The results of these tests are expressed as an average of the results for the replicates and are summarized in Table 2.

In the aforedescribed tests, phytotoxicities below about 20-30% are generally not considered meaningful because generally the plant can grow out of this amount of injury.

The compounds tested are identified by structured formats in Table A, hereinbelow.

TABLE A

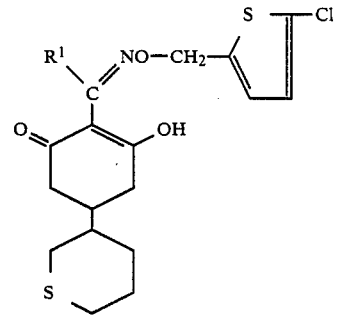

| Compound Test No. | $R^1$ |
|---|---|
| 1 | —$CH_3$ |
| C-1* | —$CH_2CH_3$ |
| C-2* | —$CH_2CH_2CH_3$ |

*C-numbers indicate comparison compounds

TABLE 1
Pre-Emergence Herbicidal Activity - Percent Control[1]
Low Dosage Tests

| Compound No. | Dosage $\gamma/cm^2$ | Crabgrass | Barnyard Grass** | Wild Oats | Rhizome Johnson-Grass*** | Yellow Foxtail | Cheat Grass | Blackgrass | Goosegrass |
|---|---|---|---|---|---|---|---|---|---|
| 1 | 0.70 | 100 | 100 | 65 | — | 100 | 0 | 100 | 100 |
| 1 | 0.28 | 100 | 95 | 0 | — | 75 | 0 | 65 | 99 |
| 1 | 0.11 | 15 | 20 | 0 | — | 15 | 0 | 0 | 57 |
| 1 | 0.04 | 0 | 0 | 0 | — | 0 | 0 | 0 | 0 |
| C-1 | 0.70 | 99 | 100 | 45 | — | 100 | 0 | 97 | 100 |
| C-1 | 0.28 | 72 | 60 | 0 | — | 90 | 0 | 30 | 90 |
| C-1 | 0.11 | 0 | 0 | 0 | — | 0 | 0 | 0 | 30 |
| C-1 | 0.04 | 0 | 0 | 0 | — | 0 | 0 | 0 | 0 |
| C-2 | 0.70 | 100 | 100 | 15 | — | 100 | 0 | 85 | 100 |
| C-2 | 0.28 | 67 | 70 | 0 | — | 55 | 0 | 25 | 79 |
| C-2 | 0.11 | 0 | 0 | 0 | — | 0 | 0 | 0 | 0 |
| C-2 | 0.04 | 0 | 0 | 0 | — | 0 | 0 | 0 | 0 |
| Check | | | | | | | | | |

| Compound No. | Dosage $\gamma/cm^2$* | Sprangletop | Italian Rye Grass | Fall Panicum | Proso Millet | Barley | Rice | Sorghum |
|---|---|---|---|---|---|---|---|---|
| 1 | 0.70 | 100 | 97 | — | 100 | 0 | 70 | 100 |
| 1 | 0.28 | 0 | 0 | — | 45 | 0 | 0 | 40 |
| 1 | 0.11 | 0 | 0 | — | 0 | 0 | 0 | 0 |
| 1 | 0.05 | 0 | 0 | — | 0 | 0 | 0 | 0 |
| C-1 | 0.70 | 90 | 100 | — | 100 | 0 | 50 | 87 |
| C-1 | 0.28 | 15 | 0 | — | 45 | 0 | 0 | 0 |
| C-1 | 0.11 | 0 | 0 | — | 0 | 0 | 0 | 0 |
| C-1 | 0.05 | 0 | 0 | — | 0 | 0 | 0 | 0 |
| C-2 | 0.70 | 100 | 100 | — | 100 | 0 | 0 | 0 |
| C-2 | 0.28 | 0 | 0 | — | 30 | 0 | 0 | 0 |
| C-2 | 0.11 | 0 | 0 | — | 0 | 0 | 0 | 0 |
| C-2 | 0.05 | 0 | 0 | — | 0 | 0 | 0 | 0 |

*$\gamma/cm^2$ = micrograms/square centimeter.
**California Barnyardgrass.
***Not tested.
[1]Reported as average of four replicates.

TABLE 2
Post-Emergence Herbicidal Activity - Percent Control[1]
Low Dosage Tests

| Grasses % Phytotoxicity |
|---|
| Rhizome |

TABLE 2-continued

Post-Emergence Herbicidal Activity - Percent Control[1]
Low Dosage Tests

| Compound No. | Dosage $\gamma/cm^2$* | Crabgrass | Barnyard Grass** | Wild Oats | Johnson-Grass | Yellow Foxtail | Cheat Grass | Blackgrass | Goosegrass |
|---|---|---|---|---|---|---|---|---|---|
| 1 | 0.28 | 100 | 100 | 100 | 100 | 99 | 99 | 87 | 100 |
| 1 | 0.11 | 100 | 100 | 92 | 100 | 99 | 92 | 95 | 99 |
| 1 | 0.04 | 96 | 97 | 0 | 92 | 67 | 55 | 45 | 98 |
| 1 | 0.02 | 12 | 10 | 0 | 0 | 0 | 0 | 0 | 10 |
| C-1 | 0.28 | 98 | 100 | 95 | 89 | 98 | 95 | 70 | 98 |
| C-1 | 0.11 | 90 | 80 | 10 | 30 | 92 | 30 | 60 | 85 |
| C-1 | 0.04 | 0 | 0 | 0 | 0 | 90 | 0 | 0 | 0 |
| C-1 | 0.02 | 0 | 0 | 0 | 0 | 0 | 0 | 0 | 0 |
| C-2 | 0.28 | 70 | 100 | 35 | 80 | 96 | 87 | 75 | 95 |
| C-2 | 0.11 | 0 | 100 | 30 | 20 | 92 | 55 | 20 | 85 |
| C-2 | 0.04 | 0 | 82 | 0 | 0 | 0 | 0 | 0 | 10 |
| C-2 Check | 0 | 0 | 0 | 0 | 0 | 0 | 0 | 0 | 0 |

| Compound No. | Dosage $\gamma/cm^2$* | Grasses % Phytotoxicity | | | | | |
|---|---|---|---|---|---|---|---|
| | | Sprangletop | Italian Rye Grass | Fall Panicum | Proso Millet | Field Corn*** | Sorghum*** |
| 1 | 0.28 | 98 | 99 | 99 | 100 | 100 | 100 |
| 1 | 0.11 | 52 | 95 | 97 | 95 | 100 | 99 |
| 1 | 0.04 | 0 | 40 | 90 | 55 | 85 | 60 |
| 1 | 0.02 | 0 | 0 | 10 | 0 | 5 | 0 |
| C-1 | 0.28 | 100 | 100 | 97 | 95 | 95 | 95 |
| C-1 | 0.11 | 25 | 80 | 95 | 30 | 55 | 87 |
| C-1 | 0.04 | 0 | 20 | 30 | 0 | 0 | 35 |
| C-1 | 0.02 | 0 | 0 | 20 | 0 | 0 | 0 |
| C-2 | 0.28 | 75 | 100 | 95 | 96 | 80 | 90 |
| C-2 | 0.11 | 0 | 95 | 90 | 60 | 60 | 55 |
| C-2 | 0.04 | 0 | 20 | 10 | 0 | 0 | 0 |

*$\gamma/cm^2$ = micrograms/$cm^2$.
**California Barnyardgrass.
***Field corn and sorghum presents significant weed problems where crops are rotated.
[1]Reported as average of three replicates.

TABLE 2A

CROPS
Post-Emergence Herbicidal Activity - Percent Control[1]
Low Dosage Tests

| Compound No | Dosage $\gamma/cm^2$* | Grasses % Phytotoxicity | | | Broadleaf % Phytotoxicity | | |
|---|---|---|---|---|---|---|---|
| | | Barley | Rice | Anza Wheat | Sugar Beet | Cotton | Soybean |
| 1 | 0.28 | 100 | 100 | 85 | 5 | 40 | 57 |
| 1 | 0.11 | 82 | 95 | 70 | 0 | 25 | 40 |
| 1 | 0.04 | 30 | 50 | 0 | 0 | 12 | 30 |
| 1 | 0.02 | 0 | 0 | 0 | 0 | 5 | 20 |
| C-1 | 0.28 | 99 | 96 | 65 | 2 | 7 | 10 |
| C-1 | 0.11 | 95 | 50 | 25 | 0 | 0 | 10 |
| C-1 | 0.04 | 0 | 0 | 0 | 0 | 0 | 0 |
| C-1 | 0.02 | 0 | 0 | 0 | 0 | 0 | 0 |
| C-2 | 0.28 | 99 | 50 | 70 | 0 | 7 | 30 |
| C-2 | 0.11 | 99 | 40 | 60 | 0 | 0 | 15 |
| C-2 | 0.04 | 50 | 0 | 0 | 0 | 0 | 0 |
| C-2 Check | 0 | 0 | 0 | 0 | 0 | 0 | 0 |

*$\gamma/cm^2$ = microgram/square centimeter.
[1]Reported as average of four replicates.

Based on the results shown in the above tables it can be seen that all three compounds exhibit both pre-emergent and post-emergence phytotoxicity against grasses but are substantially more active as post-emergent herbicides. (This is generally true of the class of oximecyclohexanedione herbicides and the commercial examples of the class of herbicide are primarily used as post-emergent herbicides.) From the post-emergent herbicide results shown in the tables, it can be seen that Compound 1, of the present invention, was more active than comparison Compound C-2 against thirteen of the fourteen weed grasses tested and was as active as Compound C-2 against the fourteenth. Comparison Compound C-1 was more active than Compound C-2, but, nonetheless, Compound 1 was more active than Compound C-1 against ten of the fourteen weed grasses. With respect to the remaining four grasses, Compound 1 was somewhat more active than Compound C-1 but not sufficiently so, that good control could be obtained using the next lower dosage level in the table's compound with the dosage level used form Compound C-1. The only instance were Compound C-1 was more active than Compound 1 was with respect to yellow foxtail at the 0.04 $\gamma/cm^2$ dosage rate. In the case of crabgrass, barnyardgrass, goosegrass, and Fall Panicum a dosage rate of Compound 1 of 0.04 $\gamma/cm^2$ was as effective or more effective than a dosage rate of 0.11 $\gamma/cm^2$ of Compound C-1. In the case of wild oats, rhizome Johnsongrass, cheatgrass, blackgrass, Proso millet, and field corn, a dosage rate of Compound 1 of 0.11 $\gamma$/cm$^2$ was as effective or more effective than a dosage rate of Compound C-1 of 0.28 $\gamma$/cm$^2$. The superiority in post-emergent phytotoxicity of Compound 1 was even greater with respect to Compound C-2.

EXAMPLE 7

In this example 3-acetyloxy-2-[1-[(5-chlorothien-2-yl)methoxyimino]ethyl]-5-(tetrahydro-2H-thiopyran-3-yl)-cyclohex-2-en-1-one) (Formula I, R=acetyl) was tested for post-emergent herbicide activity side-by-side with its R$^1$ is ethyl and propyl homologs, i.e., 3-acetyloxy-2-[1-[(5-chlorothien-2-yl)methoxyimino]-propyl]-5-(tetrahydro-2H-thiopyran-3-yl)-cyclohex-2-en-1-one) (C-3) and 3-acetyloxy-2-[1-[(5-chlorothien-2-yl)methoxyimino]butyl]-5-(tetrahydro-2H-thiopyran-3-yl)-cyclohex-2-en-1-one) (C-4). The tests were conducted in the same manner as described in Example 6 hereinbefore using the application rates given in Table 3 hereinabove. The results of these tests expressed as an average of the results of the replicates for a given compound and application rate are summarized in Table 3 hereinbelow. The components are identified by structure in Table B hereinbelow.

TABLE B

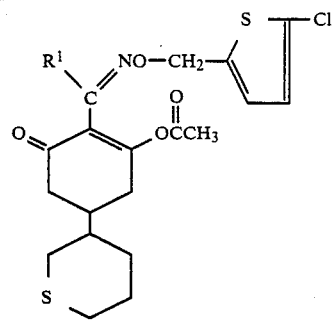

| Compound Test No. | R$^1$ |
|---|---|
| 2 | —CH$_3$ |
| C-3* | —CH$_2$CH$_3$ |
| C-4* | —CH$_2$CH$_2$CH$_3$ |

*C-numbers indicate comparison compounds

TABLE 3

Post-Emergence Herbicidal Activity - Percent Control[1]
Low-Dosage Tests

| Compound No. | Dosage $\gamma$/cm$^2$* | Grasses % Phytotoxicity | | | | | | | |
|---|---|---|---|---|---|---|---|---|---|
| | | Crabgrass | Barnyard Grass** | Wild Oats | Rhizome Johnson-Grass | Yellow Foxtail | Cheat Grass | Blackgrass | Goosegrass |
| 2 | 0.28 | 98 | 100 | 99 | 95 | 100 | 90 | 75 | 85 |
| 2 | 0.11 | 90 | 100 | 60 | 90 | 96 | 45 | 75 | 80 |
| 2 | 0.04 | 70 | 85 | 0 | 65 | 80 | 0 | 15 | 45 |
| 2 | 0.02 | 0 | 0 | 0 | 20 | 25 | 0 | 0 | 0 |
| C-3 | 0.28 | 75 | 98 | 75 | 45 | 80 | 30 | 70 | 75 |
| C-3 | 0.11 | 25 | 80 | 20 | 30 | 35 | 0 | 0 | 50 |
| C-3 | 0.04 | 0 | 0 | 0 | 0 | 0 | 0 | 0 | 0 |
| C-3 | 0.02 | 0 | 0 | 0 | 0 | 0 | 0 | 0 | 0 |
| C-4 | 0.28 | 45 | 100 | 87 | 25 | 60 | 50 | 60 | 85 |
| C-4 | 0.11 | 0 | 92 | 30 | 0 | 60 | 0 | 20 | 40 |
| C-4 | 0.04 | 0 | 50 | 0 | 0 | 0 | 0 | 0 | 0 |
| C-4 | 0.02 | 0 | 0 | 0 | 0 | 0 | 0 | 0 | 0 |
| Check | 0 | 0 | 0 | 0 | 0 | 0 | 0 | 0 | 0 |

| Compound No. | Dosage $\gamma$/cm$^2$* | Grasses % Phytotoxicity | | | | | |
|---|---|---|---|---|---|---|---|
| | | Sprangletop | Italian Rye Grass | Fall Panicum | Proso Millet | Field Corn*** | Sorghum*** |
| 2 | 0.28 | 92 | 95 | 96 | 99 | 99 | 100 |
| 2 | 0.11 | 82 | 87 | 82 | 90 | 96 | 92 |
| 2 | 0.04 | 15 | 30 | 15 | 35 | 90 | 70 |
| 2 | 0.02 | 0 | 0 | 0 | 0 | 20 | 0 |
| C-3 | 0.28 | 30 | 87 | 95 | 80 | 40 | 85 |
| C-3 | 0.11 | 0 | 30 | 35 | 40 | 20 | 30 |
| C-3 | 0.04 | 0 | 0 | 25 | 0 | 0 | 0 |
| C-3 | 0.02 | 0 | 0 | 0 | 0 | 0 | 0 |
| C-4 | 0.28 | 50 | 97 | 97 | 90 | 35 | 92 |
| C-4 | 0.11 | 0 | 70 | 72 | 35 | 0 | 30 |
| C-4 | 0.04 | 0 | 20 | 25 | 0 | 0 | 0 |
| C-4 | 0.02 | 0 | 0 | 0 | 0 | 0 | 0 |
| Check | 0 | 0 | 0 | 0 | 0 | 0 | 0 |

*$\gamma$/cm$^2$ = micrograms/cm$^2$.
**California Barnyardgrass.
***Field corn and sorghum presents significant weed problems where crops are rotated.
[1]Reported as average of three replicates.

TABLE 3A

CROPS
Post-Emergence Herbicidal Activity - Precent Control[1]

Low Dosage Tests

| Compound No | Dosage $\gamma/cm^2$* | Grasses % Phytotoxicity | | | Broadleaf % Phytotoxicity | | |
|---|---|---|---|---|---|---|---|
| | | Barley | Rice | Anza Wheat | Sugar Beet | Cotton | Soybean |
| 2 | 0.28 | 98 | 100 | 98 | 0 | 5 | 40 |
| 2 | 0.11 | 50 | 99 | 80 | 0 | 0 | 10 |
| 2 | 0.04 | 0 | 30 | 20 | 0 | 0 | 0 |
| 2 | 0.02 | 0 | 0 | 0 | 0 | 0 | 0 |
| C-3 | 0.28 | 95 | 75 | 75 | 0 | 0 | 5 |
| C-3 | 0.11 | 30 | 20 | 0 | 0 | 0 | 1 |
| C-3 | 0.04 | 0 | 0 | 0 | 0 | 0 | 0 |
| C-3 | 0.02 | 0 | 0 | 0 | 0 | 0 | 0 |
| C-4 | 0.28 | 95 | 85 | 90 | 0 | 0 | 0 |
| C-4 | 0.11 | 50 | 20 | 50 | 0 | 0 | 0 |
| C-4 | 0.04 | 0 | 0 | 0 | 0 | 0 | 0 |
| C-4 | 0.02 | 0 | 0 | 0 | 0 | 0 | 0 |
| Check | | 0 | 0 | 0 | 0 | 0 | 0 |

*$\gamma/cm^2$ = microgram/square centimeter.
[1] Reported as average of four replicates.

From the results of the above test, it can be seen that Compound 2 was substantially more active than Compound C-3 against all fourteen of the weed grasses in the test and was substantially more active than Compound C-4 against twelve of the weed grasses and was at least as active as Compound C-4 with respect to the remaining two.

EXAMPLE 8

In this example, the compounds identified in Table C were respectively tested using the procedures described hereinbelow for pre-emergent and post-emergent activity against a variety of grasses and broad-leaf plants including one grain crop and one broad-leaf crop. The compounds tested are identified by compound number in Table C hereinbelow and were prepared using the general procedures described hereinabove.

Pre-Emergent Herbicide Test

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a nonionic surfactant was added to the solution. The stock solution was then added to the appropriate amount of water, contained the same nonionic surfactant at a concentration of 625 mg/l, to give the desired test compound concentration in the spray solution.

Seeds of the test vegetation were planted in a pot of soil and the test solution was sprayed uniformly onto the soil surface at a dose of 4.4 micrograms/cm$^2$ unless otherwise specified in the following tables. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests are summarized in Table 4.

Post-Emergent Herbicidal Test

The test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) at a dose of 4.4 microgram/cm$^2$ unless otherwise specified in the following tables. After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity, 100 representing complete kill. The results of these tests are summarized in Table 5.

TABLE C

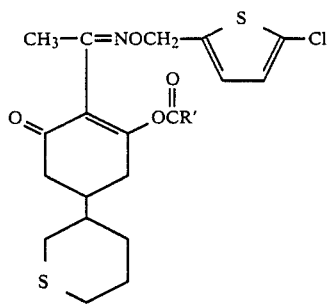

| Compound No. | R' | Appearance | Proton Chemical Shift δ in ppm (CDCl₃) | *IR (neat) in cm⁻¹ |
|---|---|---|---|---|
| 2 | CH₃ | pale yellow oil | 1.00–2.60 (m, 14H), 1.93 (s, 3H), 2.00 (s, 3H), 5.07 (s, 2H), 6.73 (s, 2H) | 1775 |
| 3 | CH₃CH₂— | pale yellow oil | 1.10 (t, 3H), 1.00–2.60 (m, 16H), 1.93 (s, 3H), 5.10 (s, 2H), 6.77 (s, 2H) | 1775 |
| 4 | CH₃(CH₂)₂— | pale yellow oil | 0.93 (t, 3H), 1.00–2.70 (m, 18H), 1.92 (s, 3H), 5.07 (s, 2H), 6.73 (s, 2H) | 1770 |
| 5 | CH₃(CH₂)₃— | pale yellow oil | 0.92 (t, 3H), 1.00–2.60 (m, 20H), 1.93 (s, 3H), 5.10 (s, 2H), 6.78 (s, 2H) | 1775 |
| 6 | (CH₃)₂CHCH₂— | pale yellow oil | 0.80–2.60 (m, 20H), 1.92 (s, 3H), 5.08 (s, 2H), 6.77 (s, 2H) | 1775 |
| 7 | CH₃(CH₂)₄— | pale yellow oil | 0.89 (t, 3H), 1.00–2.70 (m, 22H), 1.92 (s, 3H), 5.09 (s, 2H), 6.78 (s, 2H) | 1770 |
| 8 | CH₃(CH₂)₃(C₂H₅)CH— | pale yellow oil | 0.90 (t, 6H), 1.00–2.70 (m, 23H), 1.91 (s, 3H), 5.07 (s, 2H), 6.75 (s, 2H) | 1770 |

TABLE 4

Pre-Emergence Herbicidal Activity
Application Rate: 4.4 micrograms/cm², unless otherwise noted

| Compound No. | Broadleaf Plants % Phytotoxicity | | | | Grasses % Phytotoxicity | | | |
|---|---|---|---|---|---|---|---|---|
| | Lambsquarter | Mustard | Pigweed | Soybean | Barnyard Grass | Crabgrass | Wild Oats | Rice |
| 2 | 100 | 90 | 95 | 95 | 100 | 100 | 100 | 100 |
| 3 | 100 | 80 | 70 | 95 | 100 | 100 | 99 | 100 |
| 4 | 100 | 80 | 90 | 95 | 100 | 100 | 100 | 100 |
| 5 | — | 90 | 0 | 95 | 100 | 100 | — | 100 |
| 6 | 100 | 90 | 20 | 95 | 100 | 100 | 100 | 100 |
| 7 | 98 | 98 | 98 | 95 | 100 | 100 | 100 | 100 |
| 8 | 80 | 60 | 30 | 70 | 100 | 100 | 100 | 100 |

TABLE 5

Post-Emergence Herbicidal Activity
Application Rate: 4.4 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Barnyard Grass | Crabgrass | Wild Oats | Rice |
| 2 | 30 | 60 | 50 | 90 | 100 | 100 | 100 | 100 |
| 3 | 20 | 70 | 30 | 90 | 100 | 100 | 100 | 100 |
| 4 | 20 | 70 | 80 | 90 | 100 | 100 | 100 | 100 |
| 5 | 40 | 70 | 30 | 95 | 100 | 100 | 100 | 100 |
| 6 | 30 | 80 | 60 | 90 | 100 | 100 | 98 | 100 |
| 7 | 20 | 80 | 70 | 90 | 100 | 100 | 100 | 100 |
| 8 | 60 | 70 | 60 | 95 | 100 | 100 | 100 | 100 |

What is claimed is:

1. A compound having the formula:

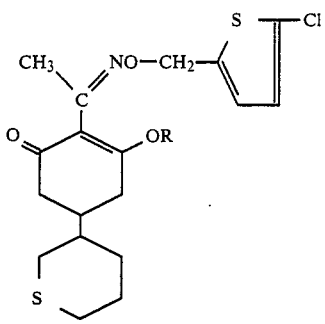

wherein R is hydrogen or

wherein R' is alkyl having 1 through 10 carbon atoms; or a compatible salt thereof.

2. The compound of claim 1 wherein R is hydrogen or a compatible salt thereof.

3. The compound of claim 1 wherein said compound is 2-(1-((5-chlorothien-2-yl)methoxyimino)ethyl)-3-hydroxy-5-(tetrahydro-2H-thiopyran-3-yl)-cyclohex-2-en-1-one.

4. The compound of claim 1 wherein R is

and R' is as defined in claim 1.

5. The compound of claim 4 wherein R' is alkyl having 1 through 6 carbon atoms.

6. The compound of claim 4 wherein said compound is 3-acetyloxy-2-(1-((5-chlorothien-2-yl)methoxyimino)ethyl)-5-(tetrahydro-2H-thiopyran-3-yl)-cyclohex-2-en-1-one.

7. A composition useful for controlling post emergent grassy weeds in sugar beet crops comprising a post emergent grassy weed herbicidally effective amount of a compound according to claim 1, and an agriculturally acceptable carrier.

8. A composition useful for controlling post emergent grassy weeds in sugar beet crops comprising a post emergent grassy weed herbicidally effective amount of a compound according to claim 2, and an agriculturally acceptable carrier.

9. A composition useful for controlling post emergent grassy weeds in sugar beet crops comprising a post emergent grassy weed herbicidally effective amount of a compound according to claim 3, and an agriculturally acceptable carrier.

10. A composition useful for controlling post emergent grassy weeds in sugar beet crops comprising a post emergent grassy weed herbicidally effective amount of a compound according to claim 4, and an agriculturally acceptable carrier.

11. A composition useful for controlling post emergent grassy weeds in sugar beet crops comprising a post emergent grassy weed herbicidally effective amount of a compound according to claim 1 and a crop oil selected from the group consisting of soybean oils, paraffinic oils, olefinic oils and mixtures thereof.

12. A method for controlling post emergent grassy plants in sugar beet crops which comprises applying a post emergent grassy weed herbicidally effective amount of a compound according to claim 1, or mixtures thereof, to the foliage or habitat of said plants.

13. A method for controlling post emergent grassy plants in sugar beet crops which comprises applying a post emergent grassy weed herbicidally effective amount of the compound according to claim 2, or mixtures thereof, to the foliage or habitat of said plants.

14. A method for controlling post emergent grassy plants in sugar beet crops which comprises applying a post emergent grassy weed herbicidally effective amount of a compound according to claim 4, or mixtures thereof, to the foliage or habitat of said plants.

15. A method for controlling post emergent the grass species of foxtail, Bermudagrass, volunteer sorghum, broad-lead signalgrass, goosegrass, red rice, sprangletop, Johnsongrass or volunteer corn in sugar beet crops which comprises applying a herbicidally effective amount of the compound of claim 2 to said grass species or their habitat.

16. A composition useful for controlling post emergent grassy weeds in sugar beet crops comprising 0.02–0.6 wt. % of a compound according to claim 1; 0.001–0.15 wt. % of an emulsifier; 0.08–2.5 wt. % of an organic solvent about 95 to 99 wt. % water.

17. The composition of claim 16 wherein said composition useful for controlling post emergent grassy weeds in sugar beet crops comprises about 0.25–2 wt. % of a crop oil selected from the group consisting of soybean oils, paraffinic oils, olefinic oils and mixtures thereof.

18. A concentrate composition useful for controlling post emergent grassy weeds in sugar beet crops comprising 23–27 wt. % of a compound according to claim 1; 2 to 4 wt. % of an emulsifier and about 70–75 wt. % of an organic solvent.

19. A method for controlling post emergent grassy plants in sugar beet crops which comprises applying a herbicidally effective amount of the compound of claim 3, to the foliage or habitat of said plants.

* * * * *